(12) United States Patent
Fiorini et al.

(10) Patent No.: US 9,038,564 B2
(45) Date of Patent: May 26, 2015

(54) METHOD FOR PERFUSING A BIOCOMPATIBLE MATERIAL GRAFT WITH A LIQUID AND PERFUSION KIT

(75) Inventors: Mauro Fiorini, Funo di Argelato (IT); Daniele Pressato, Montegrotto Terme (IT)

(73) Assignee: FIN-CERAMICA FAENZA S.P.A., Faenza (IT)

( * ) Notice: Subject to any disclaimer, the term of this patent is extended or adjusted under 35 U.S.C. 154(b) by 974 days.

(21) Appl. No.: 12/936,435

(22) PCT Filed: Apr. 8, 2009

(86) PCT No.: PCT/IB2009/005208
§ 371 (c)(1),
(2), (4) Date: Nov. 5, 2010

(87) PCT Pub. No.: WO2009/125282
PCT Pub. Date: Oct. 15, 2009

(65) Prior Publication Data
US 2011/0045163 A1 Feb. 24, 2011

(30) Foreign Application Priority Data
Apr. 11, 2008 (IT) .............................. MI2008A0643

(51) Int. Cl.
*A61L 33/00* (2006.01)
*A61F 2/46* (2006.01)
(52) U.S. Cl.
CPC .................................... *A61F 2/4644* (2013.01)
(58) Field of Classification Search
USPC .......................................... 427/2.24; 118/50
See application file for complete search history.

(56) References Cited

U.S. PATENT DOCUMENTS

| 1,551,159 | A | * | 8/1925 | Kulik ............................ 604/241 |
| 6,981,948 | B2 | | 1/2006 | Pellegrino et al. |
| 7,198,150 | B1 | | 4/2007 | Blaschke et al. |
| 2003/0190596 | A1 | | 10/2003 | Brandt et al. |
| 2004/0097828 | A1 | | 5/2004 | Pellegrino et al. |

(Continued)

FOREIGN PATENT DOCUMENTS

| EP | 1419739 A1 | | 5/2004 | |
| WO | 2005/014068 A1 | | 2/2005 | |
| WO | WO2005/014068 | * | 2/2005 | ............. A61L 24/00 |
| WO | 2005/037136 A2 | | 4/2005 | |
| WO | 2007/048016 A2 | | 4/2007 | |

*Primary Examiner* — Dah-Wei D Yuan
*Assistant Examiner* — Andrew Bowman
(74) *Attorney, Agent, or Firm* — Pearne & Gordon LLP

(57) ABSTRACT

A method for perfusing a biocompatible material graft with a perfusion liquid includes the steps of: introducing the graft (100) in a perfusion chamber (2), arranging a transfer chamber (3) partly filled with the perfusion liquid (101), coupling in a tight manner the perfusion chamber (2) and the transfer chamber (3) for establishing a fluid communication between them, lowering the pressure in the transfer chamber (3) for transferring therein part of the air existing in the perfusion chamber (2), increasing the pressure within the transfer chamber (3) for injecting in the perfusion chamber (2) the perfusion liquid (101) existing in the transfer chamber (3). A perfusion kit includes a perfusion chamber (2) apt to contain a graft (100) to be perfused with a liquid (101) and a transfer chamber (3) apt to contain a liquid (101) to be perfused, the perfusion chamber (2) being connectable in a tight manner with the transfer chamber (3) for allowing a fluid exchange between the two chambers (2, 3) and inhibiting a fluid exchange between the two chambers (2, 3) and the external environment.

9 Claims, 4 Drawing Sheets

(56) References Cited

U.S. PATENT DOCUMENTS

Figure 1:
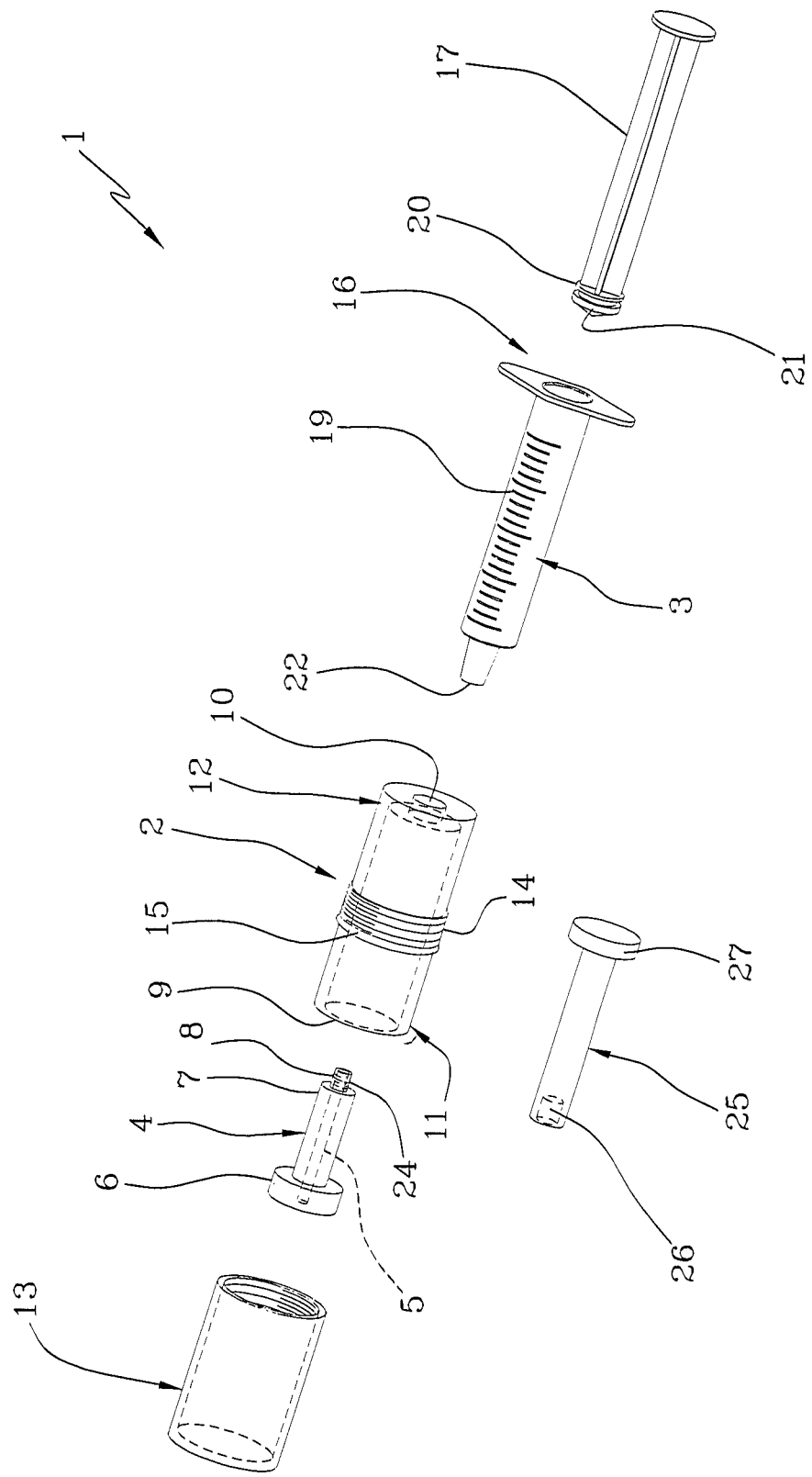

| | | |
|---|---|---|
| 2005/0288605 A1 | 12/2005 | Pellegrino et al. |
| 2006/0153001 A1 | 7/2006 | Hoerger et al. |
| 2006/0154231 A1 | 7/2006 | Brandt et al. |
| 2008/0214998 A1 | 9/2008 | Kurek et al. |
| 2009/0022878 A1 | 1/2009 | Hoerger et al. |

* cited by examiner

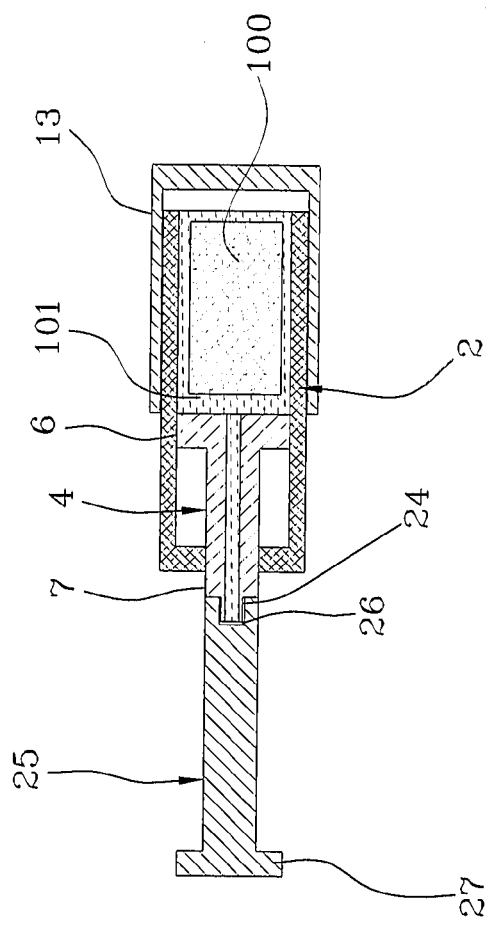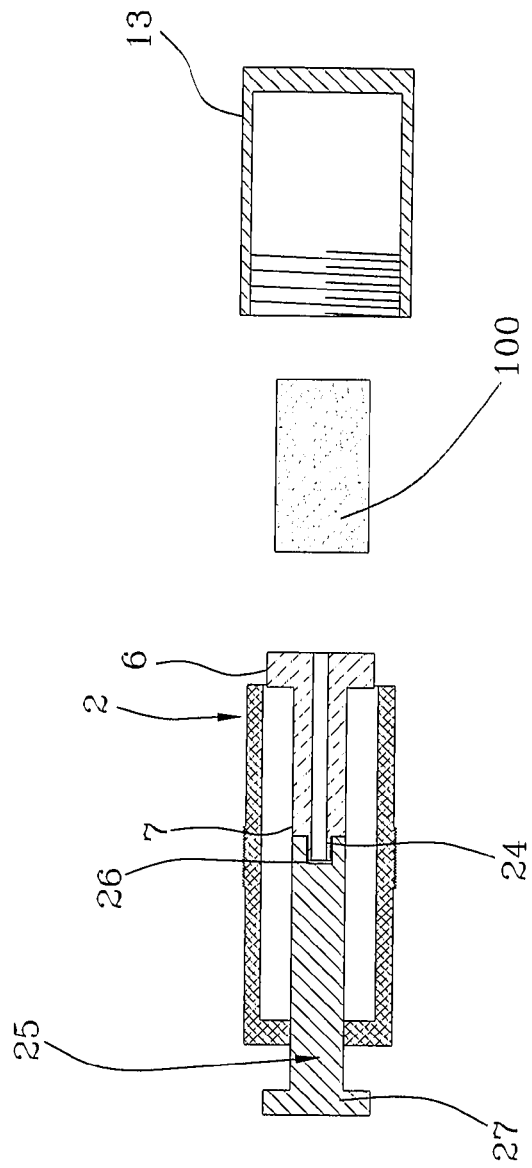
FIG 5
FIG 6

METHOD FOR PERFUSING A BIOCOMPATIBLE MATERIAL GRAFT WITH A LIQUID AND PERFUSION KIT

The present invention relates to a method for perfusing a biocompatible material graft with a liquid and a perfusion kit.

In the context of the present invention, by "biocompatible material grafts" are intended prosthetic elements made of a material of a natural or synthetic origin apt to be implanted in a living creature in order to compensate for lacunas of a bone, osteo-cartilage and/or cartilage tissue.

In the field of the orthopedic surgery, the surgeon often has to face cases in which the patient has more or less extended bone, osteo-cartilage or cartilage lacunas. Such lacunas can result from multiple causes, such as an imperfect bone reunification following to fractures, consolidation delays, malignant pathologies, infection outcomes, comminuted or multi-fragmented fractures, neonatal deformities, structural alterations of a traumatic origin, or other.

In order to face the lack of bone volume, various solutions have been proposed, in particular different substances of a natural, semi-synthetic or only synthetic origin functioning as bone, osteo-cartilage or cartilage substitute have been used. However, several authors have shown that the extraordinary mechanical behavior of the natural bone due to its nanocomposite hierarchical structure is difficult to reach with any other type of biomaterial. Therefore, the ideal bone substitute is the autologous bone withdrawn by the same patient from a donor site. This practice, however, is not free from patient risks which very often result in a resorption of the bone implant itself and a frequent occurrence of a painful symptomotology in the site in which the bone graft has been withdrawn. Recent studies have shown that the use of allogenic bone from a tissue bank of a human origin, processed and made inert through physical-chemical processes, can represent an alternative to the use of the autologous bone. However, also in this practice risks concerned to the contraction of infective diseases or immune-type reactions can subsist.

New biomaterials having functions of bone substitutes have been studied and proposed for a clinical use, and some of them have shown positive results following to clinical examinations on humans. Such materials do not simply show high biocompatibility properties (inert biomaterials), but posses biomimetic features, namely chemical and physical-chemical properties similar to the human bone capable of activating biological mechanisms (bioactivities) with the recipient bone tissues and the cell components contained therein, by promoting the neo-formation and bone consolidation processes. Once their stimulation function of the bone new formation is ended, these materials presents sometimes a complete resorption, only leaving space to the new formed bone.

As it is known, before being implanted in a patient, the above grafts are usually perfused with biological liquids or aqueous solutions of a different nature (in particular bone marrow, medullary concentrate, peripheral blood, antibiotic solutions, etc.) for creating the suitable conditions for the subsequent development of osteointegration processes.

Grafts of a biocompatible material are generally porous in order to increase their biomimetic ability. However, the presence of such porosity makes a complete perfusion from the liquid difficult to obtain, above all when this has a high viscosity. This exposes to the risk of an incomplete removal of the air existing within the graft. Such occurrence can compromise the success of the implant operation, as the presence of air can reduce the mechanical resistance of the bone grafts, interfere with the proper osteointegration and trigger tissue osteolysis and necrosis processes.

Perfusion kits are known, such as for example the one described in the WO 2007/048016 document, including a cylindrical perfusion chamber, intended for receiving the graft to be perfused, which is coupled, through a first opening, to a syringe containing a perfusion liquid. A second opening, opposite to the first one, is engaged by a plunger having a head equipped with one or more passages for placing in a fluid communication the inside of the perfusion chamber with the external environment.

The liquid in the syringe is then injected in the perfusion chamber, causing a pressure increase therein. The air, which is gradually compressed by the introduction of the perfusion liquid, is evacuated in the external environment through the passages in the plunger head inserted within the second opening of the perfusion chamber. In this way, the air existing in the pores of the graft is evacuated during the filling of the pores with the perfusion liquid. The syringe is then removed from the first opening in the perfusion chamber and the opening is sealed.

Near the first opening a third opening is foreseen, which put into fluid communication the inside of the perfusion chamber with the external environment. Such third opening has a septum which is permeable to the air and impermeable to the biological liquid. When the syringe has been removed, the plunger is pressed in the direction of the third opening by increasing the pressure within the perfusion chamber and evacuating the air, if any, still existing within the same through the septum placed on the third opening.

Another known type of a perfusion kit, such as for example the one described in the EP 1 419 739 A1 document includes a perfusion chamber within which the graft is introduced. The perfusion chamber includes an inlet arranged upstream of the graft and associated with a sort of a surgical needle having a back vent apt to allow the fluid passage from the needle to the perfusion chamber and to inhibit the fluid passage between the perfusion chamber and the needle. The perfusion chamber is further equipped with an outlet placed downstream of the graft and coupled with a pump discharging in a fluid collection basin. In use, the biological liquid is withdrawn by the surgical needle (for example from the body of a patient) and returned by the pump within the perfusion chamber. The liquid floods the perfusion chamber and exits, passing through and perfusing the graft, from the outlet for collecting itself within the collection basin. Also in this case the air is evacuated from the graft during the filling of the perfusion chamber with the perfusion liquid.

Perfusion kits and methods for perfusing biocompatible material grafts known in the art show some drawbacks. First of all, perfusion kits of the known art show perfusion chambers having a predetermined volume independently from the dimensions of the graft which has to be perfused. Therefore, in some cases, especially when the graft has reduced dimensions, there is a waste of perfusion liquid (which very often is a valuable biological liquid, as directly withdrawn by the patient in a limited quantity) due to the need of however filling the perfusion chamber independently from the dimension of the graft.

Furthermore, in the perfusion methods of the known art it is possible that a non negligible quantity of air is dissolved in the perfusion liquid during the filling of the perfusion chamber.

In fact, as said, during the filling of the perfusion chamber with the perfusion liquid, the pressure within the chamber itself increases. Such pressure increase causes an increase of the ability of the air to mix with the liquid. When the pressure is reduced, namely after the perfusion is complete, the air can again separate and remain trapped within the graft now perfused and ready for the surgical implantation.

In this context, the main technical task of the present invention is to provide a method for perfusing a biocompatible material graft with a perfusion liquid and the perfusion kit thereof apt to perform such method capable of overcoming the drawbacks above mentioned.

In the ambit of said technical task, an important object of the invention is to propose a method for perfusing a biocompatible material graft with a perfusion liquid and the perfusion kit thereof which are capable of optimizing the quantity of biological liquid to be used, with no regard to the dimensions of the graft.

A further object of the present invention is to provide a method for perfusing a biocompatible material graft with a perfusion liquid and the perfusion kit thereof capable of effectively evacuating the air from the pores of the graft itself.

The stated technical task and the specified objects are substantially achieved by a method for perfusing a biocompatible material graft with a perfusion liquid and a perfusion kit according to one or more of the appended claims.

By way of representative and not limiting example, the description of a method for perfusing a biocompatible material graft with a perfusion liquid and a perfusion kit according to the present invention is now reported, in which:

FIG. 1 shows an exploded view of a perfusion kit of a biocompatible material graft with a perfusion liquid according to the present invention; and FIGS. 2 to 6 show the kit of FIG. 1 in use in different working positions.

With reference to the enclosed figures, a perfusion kit according to the present invention has been generally shown by numeral 1.

With a particular reference to FIG. 1, the kit includes a perfusion chamber 2 apt to contain a graft 100 to be perfused and a transfer chamber 3 apt to contain a perfusion liquid 101.

The graft 100 has been outlined in the enclosed figures by a cylinder, however the graft 100 to be perfused can be in any forms and dimensions apt to the specific implant to which it is intended.

The graft 100 generally includes a biocompatible material of a natural or synthetic origin, of organic, inorganic or composite nature, which is capable of incorporating liquids, having a typical porous or fibrous (in woven or non woven form), preferably hydrophilic structure.

Examples of biocompatible materials commonly used are: calcium phosphate-based ceramic materials, for example hydroxylapatite (HA), tricalcium phosphate (alpha or beta TCP) or dicalcium phosphate (HA/TCP in different relative %); bone, osteo-cartilage and cartilage substitutes of a homologous, heterologous or biopolymeric origin (for example, hyaluronic acid-based and derivatives); materials of an autologous origin withdrawn by donor sites.

Such materials can be associated with biopolymers so as to form composite materials. Examples of biopolymers are: poly-lactic acid (PLA), poly-l-lactic acid (PLLA), polyglycolic acid (PGA), collagen, alginate, hyaluronic acid and its derivatives, carboxymethyl cellulose (CMC) and its derivatives, such as for example hydroxypropylmethyl cellulose (HPMC) or hydroxyethyl cellulose (HEC).

As for the perfusion liquid, this can consist, for example, of biological liquids or aqueous solutions of a different nature, such as for example: physiological saline, bone marrow, medullary concentrate, peripheral blood, platelet concentrate, antibiotic solutions, stem cell suspensions, growth factors or other biologically active elements apt to promote the graft osteointegration.

The perfusion chamber 2 and the transfer chamber 3 are connectable between them in a fluid-tight manner to be able to transfer the liquid contained in the transfer chamber 3 within the perfusion chamber 2, as it will be more evident in the following of the present description.

The kit 1 further includes a connection 4 which can be directly coupled with the transfer chamber 3 and inserted within the perfusion chamber 2.

The connection 4 put in fluid communication the transfer chamber 3 with the perfusion chamber 2. For this end, the connection 4 has a through hole 5 which develops itself starting from a first portion 6 until a second portion 7, arranged opposite relative to the first one 6 of the connection 4, therefore passing through the entire connection 4.

The connection 4 can be slideably introduced within the perfusion chamber 2. In particular, the first portion 6 of the connection 4 can be slideably coupled within the perfusion chamber 2 and is countershaped at the internal walls of the perfusion walls 2.

The movable coupling of the first portion 6 of the connection 4 with the perfusion chamber 2 is made in a fluid-tight manner, in such a way that any fluids, both gas and liquid, cannot pass between the connection 4 and the internal walls of the perfusion chamber 2.

The second portion 7 of the connection has an end 8 apt to be restrained to the transfer chamber 3.

The perfusion chamber 2 includes a first 9 and a second 10 openings, respectively arranged at a first 11 and a second 12 ends of the perfusion chamber 2. The first opening 9 is apt to allow the introduction of the graft 100 within the perfusion chamber 2, while the second opening 10 is apt to allow the passage of the second end 7 of the connection 4.

The kit includes a closing element 13 for closing in a fluid-tight manner the first opening 9 of the perfusion chamber 2 once the graft 100 has been introduced therein.

In the preferred embodiment of the invention, the perfusion chamber 2 is a hollow cylinder, preferably made of a plastic material.

The closing element 13 can consist, for example, of a screw stopper having a diameter greater than the diameter of the cylinder constituting the perfusion chamber 2. On the external wall of the cylinder a thread 14 engageable by the screw stopper for closing the first opening of the hollow cylinder is preferably provided.

In the proximity of the tread 14 on the cylinder, a toroidal gasket 15, which ensures the fluid-tight closing of the screw stopper 13 on the cylinder forming the perfusion chamber 2, is preferably provided.

In this embodiment, the first portion 6 of the connection 4 has a cylindrical form, whose external wall is intended for sliding in a fluid-tight manner on the internal wall of the cylinder which forms the perfusion chamber 2.

The second opening 10 of the perfusion chamber 2 has a passage section lower than the diameter of the hollow cylinder, in such a way that the first portion 6 of the connection 4 is not able, by sliding within the hollow cylinder, to exit from the perfusion chamber 2 through the second opening 10 thereof.

Also the second portion 7 of the connection 4 has a cylindrical form having a diameter slightly lower than the diameter of the second opening 10 of the perfusion chamber 2, in such a way that the connection 4 can partly exit from the perfusion chamber 2 through the second opening 10.

As above shown, the presence of the first portion 6, however, prevents the connection 4 from completely exiting through the second opening 10. On the contrary, the connection 4 can completely exit from the perfusion chamber 4 trough the first opening 9.

The transfer chamber 3 has the feature of being able to increase or decrease its own volume, due to reasons that will result apparent below.

In the preferred embodiment of the invention, the transfer chamber 3 is made by a syringe 16.

In particular, the transfer chamber 3 is formed by the volume existing between a plunger 17 of the syringe 16 and the bottom wall 18 of the cylindrical element 19 which constitutes the body of the syringe 16.

More particularly, the cylindrical element 19 of the syringe 16 includes an opening through which the plunger 17 is introduced. This latter has a head 20 having a fluid-tight sliding gasket 21 relative to the internal wall of the cylinder 19, in such a way that any fluids, both gas and liquid, cannot pass between the head 20 and the internal wall of the cylinder 19. The bottom wall 18 of the cylindrical element 19 is placed opposite relative to the opening within which the plunger 17 is introduced.

The space between the bottom wall 18 and the head 20 of the plunger defines the transfer chamber 3.

The bottom wall 18 is further equipped with an opening 22 through which the transfer chamber 3 is placed into a fluid communication with the perfusion chamber 2. In particular, the opening 22 can be coupled with the second portion 7 of the connection 4.

In order to ensure a stable coupling between the transfer chamber 3 and the connection 4, the opening 22 of the syringe includes an internally threaded cylindrical portion 23 which engages a thread 24 placed at one end of the second portion 7 of the connection 4. Such thread 24 partly surrounds the hole 5 which passes through the connection 4.

The kit further includes an extractor 25 to discharge the graft 100 from the perfusion chamber 2 when the graft 100 has been perfused of liquid.

The extractor 25 can be coupled to the second end 7 of the connection 4 for pushing the first end 6 of the connection 4 towards the first opening 9 of the perfusion chamber 2. In particular, the extractor 25 includes a first threaded end 26 which can be screwed on the second end 7 of the connection 4.

The extractor further includes a second end 27, opposite to the first one 26, having cross dimensions greater than the diameter of the cylinder constituting the perfusion chamber 2.

A method for perfusing a biocompatible material graft with a perfusion liquid according to the present invention will be now described.

For the sake of explanatory clarity, a method carried out by the perfusion kit above described will be discussed, which constitutes a preferred but not exclusive implementation means of the method itself.

The method for perfusing a biocompatible material graft with a perfusion liquid includes the steps of introducing a graft in a perfusion chamber 2, arranging a transfer chamber 3 partly filled with a perfusion liquid 101 and coupling in a fluid-tight manner the perfusion chamber 2 and the transfer chamber 3, for establishing a fluid communication among the two. The method then provides the lowering of the pressure in the transfer chamber 3 for transferring within the same part of the air existing in the perfusion chamber 2 and successively the increase of the pressure within the transfer chamber 3, in order to inject in the perfusion chamber 2 the liquid 101 existing in the transfer chamber 3.

It is to be underlined that the steps of decreasing and increasing the pressure and injecting the fluid 101 are carried out under conditions of fluid isolation between the perfusion 2 and transfer 3 chambers with respect to the external environment.

In particular, the graft 100 is first introduced within the perfusion chamber 2. This operation is carried out by introducing the graft 100 through the first opening 9 of the perfusion chamber.

Before introducing the graft 100 within the perfusion chamber 2, the connection 4 is introduced therein. In particular, the connection 4 is introduced by first introducing the second portion 7 of the same and successively the first portion 6.

In this way, the second portion 7 exits from the second opening 10 of the perfusion chamber 2 and the first portion 9 engages, in a sliding and fluid-tight manner, the internal wall of the perfusion chamber 2. Next, the perfusion chamber 2 is closed by the closing element 13. Note that in this configuration, the perfusion chamber 2 has a one-way fluid communication with the external environment. Such communication way is due to the hole 5 which passes through the connection 4.

Advantageously, the connection 4 is retreated towards the graft 100 introduced within the perfusion chamber (as shown in FIGS. 2 to 5), in such a way to decrease the volume of the same within which the graft 100 is housed.

In particular, the first portion 6 of the connection 4 is slid along the internal wall of the perfusion chamber 2 and towards the first opening 9 of the same.

This allows to minimize the volume of fluid 101 required for perfusing the graft 100, as it will be more explained hereinbelow.

Figure 2:
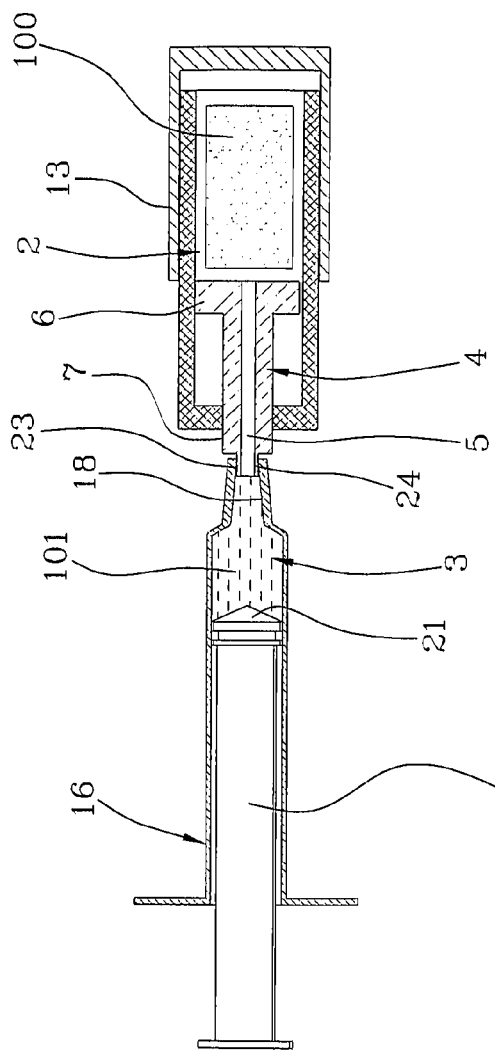
Figure 3:
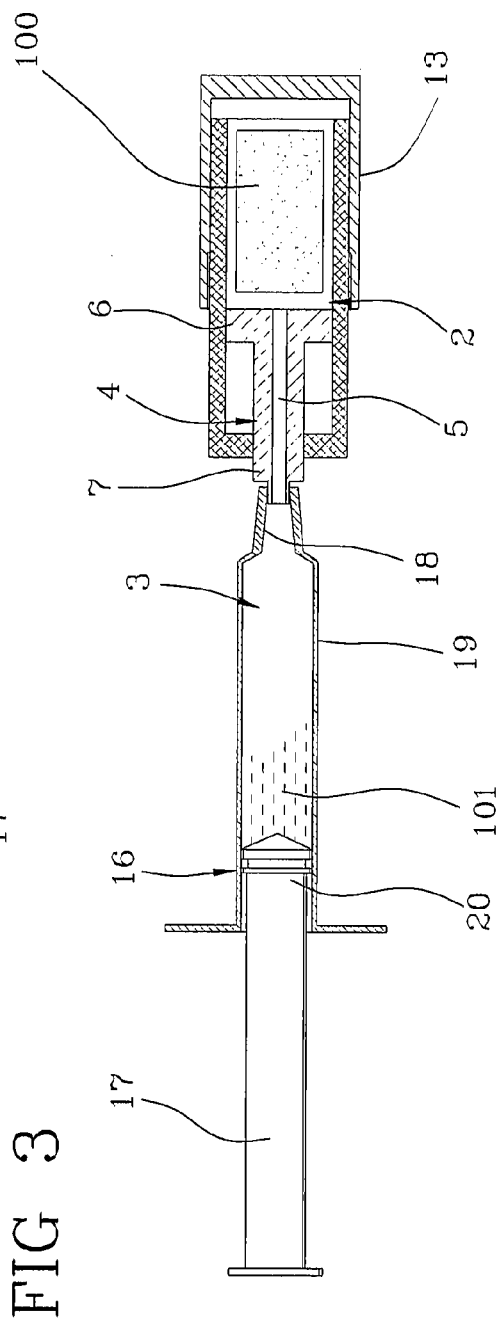

At this point, the perfusion chamber 2 is tight-coupled with the transfer chamber 3 (see FIG. 2).

This latter is preventively at least partly filled with the perfusion liquid 101, preferably by directly sucking-up the liquid from a container with the syringe 16 or directly withdrawing the same from a patient through a proper suction kit.

The fluid communication between the perfusion chamber 2 and the transfer chamber 3 is carried out through the connection 4. In particular, the second portion 7 of this latter is screwed on the threaded cylindrical element 19 of the bottom wall 18 of the syringe 16.

In this configuration, the plunger 17 is introduced within the syringe 16 for defining the transfer chamber 3 as already above described.

It is to be underlined that, in this configuration, the perfusion chamber 2 and the transfer chamber 3 are in a fluid communication between them but in a fluid isolation with the external environment.

The perfusion chamber 2 and the graft 100 are placed at the ambient pressure existing during the steps of introduction of the graft 100 within the perfusion chamber 2. Analogously, the liquid in the transfer chamber 3 is at ambient pressure.

At this point, the pressure within the transfer chamber 3 is lowered. Such pressure lowering takes places by increasing the volume of the transfer chamber 3. In the preferred embodiment, this is obtained by moving the plunger 17 of the syringe 16 away from the bottom wall 18 of the syringe 16 (see FIG. 3).

The pressure reduction in the transfer chamber 3 causes a pressure lowering in the perfusion chamber 2, in such a way to balance again the pressures within the two chambers.

The pressure lowering within the perfusion chamber 2 takes place through an air transfer from the perfusion chamber 2 to the transfer chamber 3. This inevitably causes the exit of the air existing within the pores of the graft 100.

Therefore, as a function of the degree of pressure decrease within the transfer chamber 3, namely as a function of the volume increase of the chamber itself, a significant portion of air is evacuated from the pores of the graft 100.

Next, the pressure within the transfer chamber 3 is increased for injecting the liquid 101 within the perfusion chamber 2.

The liquid 101, while entering the perfusion chamber 2 at a pressure greater than that existing within the same, permeates the pores of the graft 101 previously at least partly emptied from the air.

This operation is carried out by decreasing the volume of the transfer chamber 3. In particular, the operation is carried out by pushing the plunger 17 towards the bottom wall 18 of the syringe 16.

Figure 4:
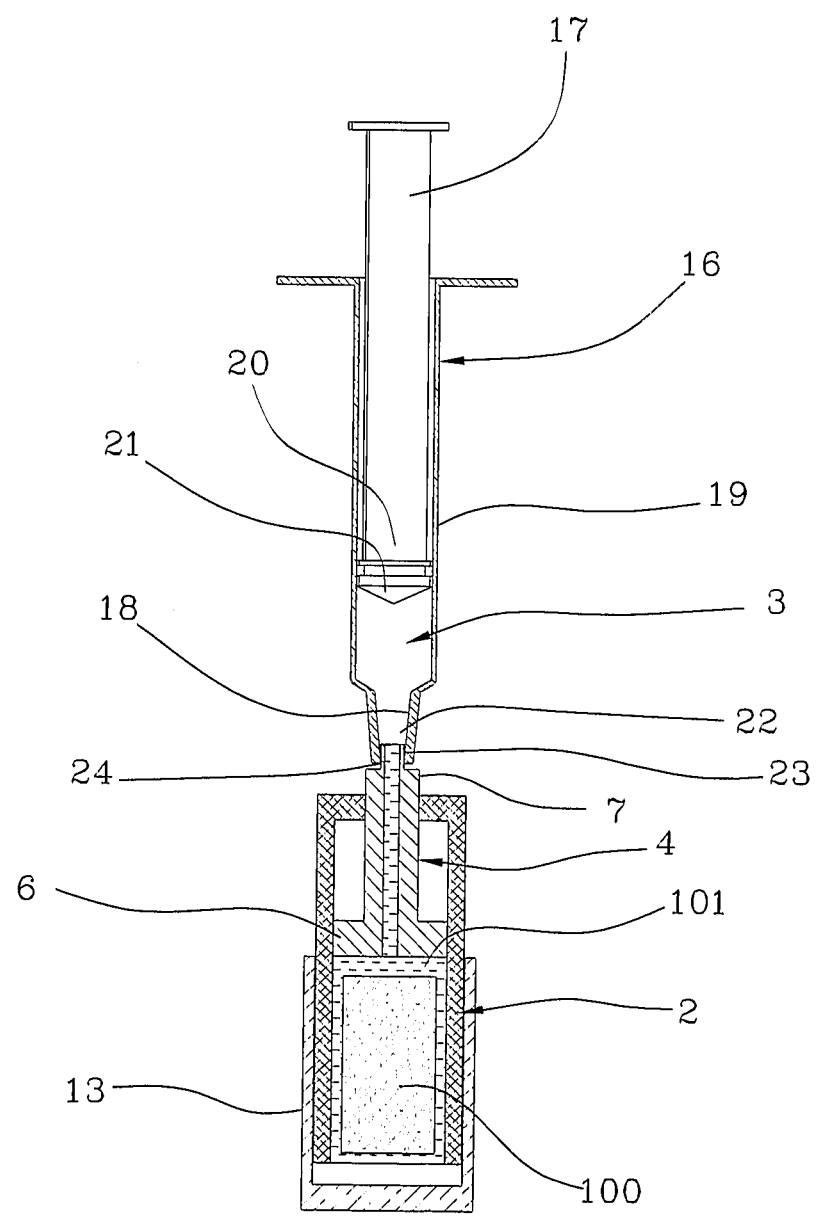

In order to avoid that during the injection of liquid 101 within the perfusion chamber 2 also the air existing in the transfer chamber 3 (previously withdrawn by the perfusion chamber 3) returns again in the perfusion chamber 2, the transfer chamber 3 and the perfusion chamber 2 are rotated for vertically arranging themselves with the transfer chamber 3 placed above the perfusion chamber 2 (see FIG. 4).

In order to increase the perfusion effectiveness of the graft 100, the pressure within the transfer chamber 3 is again lowered, with the consequent withdrawal from the perfusion chamber 2 of the liquid 101 just injected and the air, if any, still existing within the perfusion chamber and the pores of the graft 100. The pressure decrease within the transfer chamber 3 is obtained in the same way already above described.

At this point, the pressure in the transfer chamber 3 is again increased (in the same way above described) for transferring again only the liquid 101 in the perfusion chamber 2 and the pores of the graft 100.

These operations, namely the emptying and the filling with the liquid 101 of the perfusion chamber 2, are repeated until the liquid 101 is uniformly distributed within the graft 100.

The number of repetitions depends on the type of the material of the graft 100 to be perfuse, the type of liquid 101 and the dimensions of the graft 100 itself. Once the perfusion is ended, the pressure within the perfusion chamber 2 is equal to the one at the beginning of the operations, as well as the pressure within the transfer chamber 3. In fact, during all the operations of fluid transfers between the two chambers, these latter are remained isolated from the external environment.

The final effect is that the liquid existing in the transfer chamber 3 has been transferred in the perfusion chamber 2 and inside the graft 100 and that the air existing in the perfusion chamber 2 and the graft 100 has been transferred in the transfer chamber 3. Once the perfusion of the graft is ended, the transfer chamber 3 is decoupled from the perfusion chamber 2. In particular, the syringe 16 is unscrewed from the connection 4.

On the second portion 7 of the connection 4 is then mounted the extractor 25, as shown in FIG. 5. Preferably, the threaded end 26 of the extractor 25 is screwed on the second portion 7 of the connection 4. After or before this latter operation, the perfusion chamber 2 is opened in correspondence with its first opening 9. In particular, the closing element 13 is removed by the first opening of the perfusion chamber 2.

By pushing the extractor towards the first opening 9 of the perfusion chamber 2, the perfused graft 100 is pushed by the connection 4 and comes out from the first opening of the perfusion chamber 2, as shown in FIG. 6. Note that the use of the extractor prevents the perfused graft 100 from being directly handled by the operator.

The invention attains the proposed aims. In fact, the method and the kit of the present invention allow, first of all, to optimize the quantity of perfusion liquid 101 used independently from the dimensions of the graft 100, as the connection 4, being sliding in a fluid-tight manner within the perfusion chamber 2, ensures that the perfusion chamber 2 adapts its volume as a function of the dimensions of the graft 100.

Moreover, the air is effectively evacuated from the pores of the graft 100 and replaced by the liquid 101, since the air is evacuated or however the pressure thereof is remarkably reduced before the perfusion of the graft 100 by the liquid, by avoiding that air and liquid are mixed within the graft when the air has a high pressure.

Furthermore, it is to be underlined that the perfusion means of the present invention is capable of optimizing the quantity of the perfusion liquid independently from the dimensions and the configuration of the graft, up to a volume equivalent to that within the perfusion chamber.

The invention claimed is:

1. A perfusion kit including:
   a perfusion chamber apt to contain a graft to be perfused with a perfusion liquid and having a first end defining a first opening and having a second end defining a second opening;
   a transfer chamber apt to contain a liquid to be perfused, said perfusion chamber being connectable in a tight manner to said transfer chamber in order to allow a fluid exchange between the two chambers and inhibit a fluid exchange between the two chambers and the external environment; and
   a connection which can be directly coupled with the transfer chamber and movably introduced within the perfusion chamber for defining different volumes of the perfusion chamber as a function of the dimensions of the graft; said connection enabling a fluid communication between the transfer chamber and the perfusion chamber characterized in that said connection includes a first portion which can be abutted in a sliding and tight manner along an internal wall of the perfusion chamber and a second portion, opposite relative to the first one, which is extendable through the second opening so that it can be directly coupled with the transfer chamber and which has a cylindrical form having a diameter slightly lower than the diameter of the second opening of the perfusion chamber in such a way that the connection can partly exit from the perfusion chamber through the second opening, the first portion of the connection being unable to pass through the second opening; and said connection having a through hole extending from the first to the second portion to obtain a fluid communication between the two chambers.

2. A kit according to claim 1, including a closing element for closing in a fluid-tight manner the first opening of the perfusion chamber through which the graft can be introduced.

3. A kit according to claim 1, wherein the perfusion chamber is a hollow cylinder.

4. A kit according to claim 1, including an extractor for exiting the graft from the perfusion chamber when the graft has been perfused with liquid.

5. A kit according to claim 4, wherein said extractor can be coupled with the second portion of the connection for pushing the first portion of the connection towards the first opening of the perfusion chamber.

6. A kit according to claim 1, wherein said transfer chamber is defined by a volume available between a plunger of a syringe and a bottom wall of the syringe, said plunger being movable relative to the bottom wall of the syringe.

7. A kit according to claim 6, wherein said second portion of the connection and said syringe include respective threaded portions for being coupled in a fluid-tight manner.

8. A kit according to claim 7, wherein the threaded portion of the syringe is located internally in an opening of the syringe and the threaded portion of the second portion of the connection is located at an end of the second portion.

9. A method of using a perfusion kit, said perfusion kit including:
- a perfusion chamber apt to contain a graft to be perfused with a perfusion liquid and having a first end defining a first opening and having a second end defining a second opening;
- a transfer chamber apt to contain a liquid to be perfused, said perfusion chamber being connectable in a tight manner to said transfer chamber in order to allow a fluid exchange between the two chambers and inhibit a fluid exchange between the two chambers and the external environment; and
- a connection which can be directly coupled with the transfer chamber and movably introduced within the perfusion chamber for defining different volumes of the perfusion chamber as a function of the dimensions of the graft; said connection enabling a fluid communication between the transfer chamber and the perfusion chamber characterized in that said connection includes a first portion which can be abutted in a sliding and tight manner along an internal wall of the perfusion chamber and a second portion, opposite relative to the first one, which is extendable through the second opening so that it can be directly coupled with the transfer chamber and which has a cylindrical form having a diameter slightly lower than the diameter of the second opening of the perfusion chamber in such a way that the connection can partly exit from the perfusion chamber through the second opening, the first portion of the connection being unable to pass through the second opening; and said connection having a through hole extending from the first to the second portion to obtain a fluid communication between the two chambers;

said method comprising the following step:
- perfusing a biocompatible material graft with a perfusion liquid by means of said perfusion kit.

\* \* \* \* \*